United States Patent [19]

Znaiden et al.

[11] Patent Number: 5,425,938
[45] Date of Patent: Jun. 20, 1995

[54] POLYAMINO SALTS OF ALPHA-HYDROXYACIDS, ALPHA-KETOACIDS AND RELATED COMPOUNDS

[75] Inventors: Alexander P. Znaiden, Trumbull; Anthony W. Johnson, Fairfield; Brian A. Crotty, Branford, all of Conn.

[73] Assignee: Chesebrough-Pond's USA Co., Division of Conopco, Inc., Greenwich, Conn.

[21] Appl. No.: 188,519

[22] Filed: Jan. 28, 1994

[51] Int. Cl.$^6$ .................. A61K 31/74; A61K 7/02; A61K 7/32; A61K 7/027; A61K 7/48

[52] U.S. Cl. .................. 424/78.02; 424/401; 424/64; 424/65; 424/70.1; 424/70.24; 424/78.31; 424/78.32; 424/78.37; 424/59; 424/DIG. 5; 514/557; 514/558; 514/559; 514/560; 514/568; 514/569; 514/570; 514/572; 514/574; 514/844; 514/845; 514/846; 514/847; 514/848; 514/880; 514/881; 514/944

[58] Field of Search .............. 424/401, 64, 70, 78.02, 424/70.1, 70.24, 78.31, 78.32, 78.37; 514/844-848, 59, 65, DIG. 5, 880, 881, 944, 557, 558-560, 568-570, 572-574

[56] References Cited

U.S. PATENT DOCUMENTS

| | | | |
|---|---|---|---|
| 4,105,782 | 8/1978 | Yu et al. | 424/283 |
| 4,105,783 | 8/1978 | Yu et al. | 424/283 |
| 4,202,881 | 5/1980 | Gross et al. | 424/70 |
| 4,234,599 | 11/1980 | Van Scott et al. | 424/279 |
| 4,363,815 | 12/1982 | Yu et al. | 424/274 |
| 4,424,234 | 1/1984 | Alderson et al. | 424/317 |
| 4,612,331 | 9/1986 | Barratt et al. | 514/558 |
| 5,091,171 | 2/1992 | Yu et al. | 424/642 |
| 5,196,187 | 3/1993 | Nicoll et al. | 424/70 |

OTHER PUBLICATIONS

Elizabeth Arden's Ceramide Time Complex Moisture Cream–Label, 1993.

*Primary Examiner*—Jyothsna Venkat
*Attorney, Agent, or Firm*—Milton L. Honig

[57] ABSTRACT

Cosmetic compositions are described wherein α-hydroxyacids, α-ketoacids and related compounds are formed into amine salts through neutralization with a multi-amine functionalized polymer. Particularly preferred are glycolic acid and lactic acid salts of poly(ethylenimine).

8 Claims, No Drawings

POLYAMINO SALTS OF ALPHA-HYDROXYACIDS, ALPHA-KETOACIDS AND RELATED COMPOUNDS

BACKGROUND OF THE INVENTION

1. Field of the Invention

The invention concerns cosmetic compositions and methods using such compositions for topical application to human skin. More particularly, the invention concerns an improved system for the delivery of α-hydroxy compounds that overcomes formulation difficulties and improves sensory properties.

2. The Related Art

A soft, supple and flexible skin has a marked cosmetic appeal and is an attribute of normal functioning epidermis. As human skin ages with advancing years, the epidermis can become folded or ridged or furrowed to form wrinkles which signal the loss of youthful appearance and herald the transition to old age. This transition can even occur prematurely with young people, especially those who expose themselves to excessive doses of sunlight. Also, the outer layer of the epidermis, that is the stratum corneum, can become dry and flaky following exposure to cold weather, or excessive contact with detergents or solvents which result in loss of skin moisture. Thereby, skin loses its soft, supple and flexible characteristics.

Emollients such as fats, phospholipids and sterols have in the past been used to soften wrinkled or dry skin, but it is apparent that these emollients are only partially effective as a remedy for skin in poor condition.

The use of α-hydroxyacids for enhancing the quality of human skin following topical application thereto has been widely reported.

U.S. Pat. No. 4,105,782 and U.S. Pat. No. 4,105,783, both to Yu and Van Scott, disclose the use of amines or ammonium salts of α-hydroxyacids in the treatment of ache, dandruff and dry skin. U.S. Pat. No. 4,234,599 (Yu & Van Scott) proposes the use of α-hydroxyacids and their esters or amine salts in the treatment of keratoses. U.S. Pat. No. 4,363,815 (Yu & Van Scott) suggests the use of α-hydroxyacids or β-hydroxyacids or ketoacids and their derivatives, in a composition for treating skin conditions. Most recently, U.S. Pat. No. 5,091,171 (Yu & Van Scott) reports the use of α-hydroxyacids, α-ketoacids and related compounds as topically effective in the treatment of warts, nail infections, age spots, wrinkles and aging related skin changes.

U.S. Pat. No. 4,424,234 (Alderson et al.) identifies $C_6$-$C_{10}$ α-hydroxy carboxylic acids as agents for improving human skin, particularly with emphasis upon the conditions of dryness and flakiness. U.S. Pat. No. 4,612,331 (Barratt et al.) reports that α-hydroxyoctanoic acid when combined with a neutralizing agent such as an alkanolamine enhances the extensibility of the stratum corneum without the development of skin irritation normally occurring in the absence of the neutralizing agent.

Based on the foregoing disclosures, it is evident that α-hydroxyacids and α-ketoacids have been well established in the art as therapeutically effective for cosmetic and dermatologic conditions and disorders. Unfortunately, formulation chemists have had a difficult time in providing stable creams or lotions containing these compounds in their active forms. Moreover, it is also difficult to deliver these compounds to the skin in their active form without causing skin irritation.

Accordingly, it is an object of the present invention to provide a cosmetic composition stably incorporating an active form of α-hydroxyacids, α-ketoacids or related compounds in a cream or lotion.

It is another object of the present invention to provide a cosmetic composition containing α-hydroxyacids, α-ketoacids or related compounds which when applied to skin in relatively high concentrations will cause less skin irritation than previously achievable.

A still further object of the present invention is to provide a method for treating dry skin, warts, nail infections, age spots, wrinkles and aging related skin changes with compositions that are effective but impart less skin irritation than compositions utilized hitherto.

These and other objects of the present invention that will become more readily apparent from consideration of the following summary, detailed description and examples which follow.

SUMMARY OF THE INVENTION

A cosmetic composition is provided including:

(i) from about 0.01 to about 40% of an active compound selected from the group consisting of α-hydroxyacid, α-ketoacid and related compounds, tje α-hydroxyacid being at least one member selected from the group consisting of alkyl α-hydroxyacid, aralkyl and aryl α-hydroxyacid, polyhydroxy α-hydroxyacid and polycarboxylic α-hydroxyacid represented by the following chemical structure:

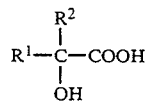

wherein $R^1$ and $R^2$ are selected from the group consisting of H, F, Cl, Br, alkyl, aralkyl and aryl radicals whether saturated or unsaturated, isomeric or nonisomeric, straight or branched chain, having 1 to 25 carbon atoms, or in cyclic form having 5 to 6 ring members, and in addition $R^1$ and $R^2$ may carry OH, CHO, COOH and alkoxy groups having 1 to 9 carbon atoms, the α-hydroxyacid existing as a free acid or lactone form, or in salt form with an organic base or an inorganic alkali, and as stereoisomers in D, L, and DL forms when $R^1$ and $R^2$ are not identical;

the α-ketoacid being at least one member selected from a group of compounds represented by the following chemical structure:

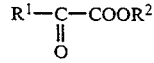

wherein $R^1$ and $R^2$ are selected from the group consisting of H, alkyl, aralkyl and aryl radicals whether saturated or unsaturated, isomeric or nonisomeric, straight or branched chain, having 1 to 25 carbon atoms, or in cyclic form having 5 to 6 ring members, and in addition $R^1$ may carry F, Cl, Br, I, OH, CHO, COOH and alkoxy groups having 1 to 9 carbon atoms, the α-ketoacid existing as a free acid or an ester form, or in a salt form with an organic base or an inorganic alkali; and the related compounds being at least one member selected from the group consisting of ascorbic acid, quinic acid, isocitric acid, tropic acid, trethocanic acid, 3-chlorolactic acid, cerebronic acid, citramalic acid, agaricic acid, 2-hydroxynervonic acid, aleuritic acid and pantoic acid;

(ii) from about 0.01 to about 40% of a multi-amine functionalized polymer, the polymer neutralizing at least some of the active compound thereby forming an amine salt thereof; and (iii) from about 1 to about 95% by weight of a pharmaceutically acceptable carrier for the amine salt.

Also provided is a method for treatment of dry skin, warts, nail infections, age spots, wrinkles and aging related skin changes that includes topically applying to skin the cosmetic compositions defined above, and which method will minimize skin irritation.

DETAILED DESCRIPTION

Now it has been discovered that α-hydroxyacids, α-ketoacids and related compounds can be more readily formulated and their skin irritation minimized when they are neutralized at least partially with a multi-amine functionalized polymer.

Thus, the first important element of the claimed invention is an active compound which is either an α-hydroxyacid, a α-ketoacid or a related compound. The active compound may be present in an amount from about 0.01 to about 40%, preferably from about 0.1% to about 20%, optimally between about 0.5 and 12% by weight.

The α-hydroxyacid may be selected from the group consisting of alkyl α-hydroxyacid, aralkyl and aryl α-hydroxyacid, polyhydroxy α-hydroxyacid and polycarboxylic α-hydroxyacid represented by the following chemical structure:

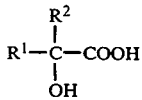

wherein $R^1$ and $R^2$ are H, F, Cl, Br, alkyl, aralkyl or aryl radicals and may either be saturated or unsaturated, isomeric or nonisomeric, straight or branched chain, having 1 to 25 carbon atoms, or cyclic in form having 5 to 6 ring members, and in addition $R^1$ and $R^2$ may carry OH, CHO, COOH and alkoxy groups having 1 to 9 carbon atoms, the α-hydroxyacid existing as a free acid or lactone form, or in salt form with an organic base or an inorganic alkali, and as stereoisomers in D, L and DL forms when $R^1$ and $R^2$ are not identical. The L form is most preferred.

Typical alkyl, aralkyl and aryl groups for $R^1$ and $R^2$ include methyl, ethyl, propyl, isopropyl, butyl, pentyl, octyl, lauryl, stearyl, benzyl and phenyl.

The α-hydroxyacids, as noted above, can be classified as (1) alkyl α-hydroxyacids, (3) aralkyl and aryl α-hydroxyacids, (3) polyhydroxy alpha hydroxyacids, and (4) polycarboxylic α-hydroxyacids. The following are representative α-hydroxyacids in each subgroup.

(1) Alkyl α-Hydroxyacids
1. 2-Hydroxyethanoic acid (Glycolic acid, hydroxyacetic acid)
(H) (H) C (OH) COOH
2. 2-Hydroxypropanoic acid (Lactic acid)
($CH_3$) (H) C (OH) COOH
3. 2-Methyl 2-hydroxypropanoic acid (Methyllactic acid)
($CH_3$) ($CH_3$) C (OH) COOH
4. 2-Hydroxybutanoic acid
($C_2H_5$) (H) C (OH) COOH
5. 2-Hydroxypentanoic acid
($C_3H_7$) (H) C (OH) COOH
6. 2-Hydroxyhexanoic acid
($C_4H_9$) (H) C (OH) COOH
7. 2-Hydroxyheptanoic acid
($C_5H_{11}$) (H) C (OH) COOH
8. 2-Hydroxyoctanoic acid
($C_6H_{13}$) (H) C (OH) COOH
9. 2-Hydroxynonanoic acid
($C_7H_{15}$) (H) C (OH) COOH
10. 2-Hydroxydecanoic acid
($C_8H_{19}$) (H) C (OH) COOH
11. 2-Hydroxyundecanoic acid
($C_9H_{19}$) (H) C (OH) COOH
12. 2-Hydroxydodecanoic acid (Alpha hydroxylauric acid)
($C_{10}H_{21}$) (H) C (OH)COOH
13. 2-Hydroxytetradecanoic acid (Alpha hydroxymyristic acid)
($C_{12}H_{25}$) (H) C (OH) COOH
14. 2-Hydroxyhexadecanoic acid (Alpha hydroxypalmitic acid)
($C_{14}H_{29}$) (H)C (OH) COOH
15. 2-Hydroxyoctadecanoic acid (Alpha hydroxystearic acid)
($C_{16}H_{34}$) (H) C (OH) COOH
16. 2-Hydroxyeicosanoic acid (Alpha hydroxyarachidonic acid)
($C_{18}H_{37}$) (H) C (OH) COOH (2) Aralkyl And Aryl Alpha Hydroxyacids
1. 2-Phenyl 2-hydroxyethanoic acid (Mandelic acid)
($C_6H_5$) (H) C (OH) COOH
2. 2,2-Diphenyl 2-hydroxyethanoic acid (Benzilic acid)
($C_6H_5$) ($C_6H_5$) C (OH) COOH
3. 3-Phenyl 2-hydroxypropanoic acid (Phenyllactic acid)
($C_6H_5CH_2$) (H) C (OH) COOH
4. 2-Phenyl 2-methyl 2-hydroxyethanoic acid (Atrolactic acid)
($C_6H_5$) ($CH_3$) C (OH) COOH
5. 2-(4'-Hydroxyphenyl) 2-hydroxyethanoic acid (4-Hydroxymandelic acid)
(HO-$C_6H_4$) (H) C (OH) COOH
6. 2-(4'-Chlorophenyl) 2-hydroxyethanoic acid (4-Chloromandelic acid)
(Cl-$C_6H_4$) (H) C (OH) COOH
7. 2-(3'-Hydroxy-4'-methoxyphenyl) 2-hydroxyethanoic acid (3-Hydroxy-4-methoxymandelic acid)
(HO-,$CH_3O$-$C_6H_3$) (H) C (OH) COOH
8. 2-(4'-Hydroxy-3'-ethoxyphenyl) 2-hydroxyethanoic acid (4-Hydroxy-3-methoxymandelic acid)
(HO-,$CH_3O$-$C_6H_3$) (H) C (OH) COOH
9. 3-(2'-Hydroxyphenyl) 2-hydroxypropanoic acid [3-(2'Hydroxyphenyl)lactic acid]
HO-$C_6H_4$-$CH_2$(H) C (OH) COOH
10. 3-(4'-Hydroxyphenyl) 2-hydroxypropanoic acid [3-(4'Hydroxyphenyl) lactic acid]
HO-$C_6H_4$-$CH_2$ (H) C (OH) COOH
11. 2-(3',4'-Dihydroxphenyl) 2-hydroxyethanoic acid (3,4'Dihydroxymandelic acid)
HO-,HO-$C_6H_3$ (H) C (OH) COOH (3) Polyhydroxy Alpha Hydroxyacids
1. 2,3-Dihydroxypropanoic acid (Glyceric acid)
(HOCH$_2$) (H) C (OH) COOH 2. 2,3,4-Trihydroxybutanoic acid, (Isomers: erythronic acid and threonic acid)
HOCH$_2$ (HO)CH$_2$(H) C (OH) COOH
3. 2,3,4,5-Tetrahydroxypentanoic acid (Isomers: ribonic acid, arabinoic acid, xylonic acid and lyxonic acid)
HOCH$_2$(HO)CH$_2$ (HO)CH$_2$(H) C (OH) COOH
4. 2,3,4,5,6-Pentahydroxyhexanoic acid (Isomers: allonic acid, altronic acid, gluconic acid, mannonic acid, gulonic acid, idonic acid, galactonic acid and talonic acid)
HOCH$_2$(HO)CH$_2$(HO)CH$_2$(HO)CH$_2$(H) C (OH) COOH
5. 2,3,4,5,6,7-Hexahydroxyheptanoic acid (Isomers: glucoheptonic acid, galactoheptonic acid, etc.)
HOCH$_2$(HO)CH$_2$(HO)CH$_2$(HO)CH$_2$(HO)CH$_2$(H) C (OH)COOH (4) Polycarboxylic Alpha Hydroxyacids
1. 2-Hydroxypropane-1,3-dioic acid (Tartronic acid)
HOOC (H) C (OH) COOH
2. 2-Hydroxybutane-1,4-dioic acid (Malic acid)
HOOC CH$_2$ (H) C (OH) COOH
3. 2,3-Dihydroxybutane-1,4-dioic acid (Tartaric acid)
HOOC (HO)CH (H) C (OH) COOH
4. 2-Hydroxy-2-carboxypentane-1,5-dioic acid (Citric acid)
HOOC CH$_2$ C (OH)(COOH)CH$_2$ COOH
5. 2,3,4,5-Tetrahydroxyhexane-1,6-dioic acid (Isomers; saccharic; acid, mucic acid, etc.)
HOOC (CHOH)$_4$COOH (5) Lactone Forms The typical lactone forms are gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

The second type of active compound according to the present invention is an organic carboxylic acid in which the alpha carbon is in keto form. The generic structure of such α-ketoacids may be represented as follows:

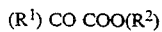

wherein R$^1$ and R$^2$ are H, alkyl, aralkyl or aryl groups that are saturated or unsaturated, isomeric or non-isomeric, straight or branched chain or in cyclic form, having 1 to 25 carbon atoms, and in addition R$^1$ may carry F, Cl, Br, I, OH, CHO, COOH and alkoxy group having 1 to 9 carbon atoms. The α-ketoacids may be present as a free acid or an ester form, or in a salt form with an organic base or an inorganic alkali. The typical alkyl, aralkyl and aryl groups for R$^1$ and R$^2$ include methyl, ethyl, propyl, isopropyl, butyl, pentyl, octyl, lauryl, stearyl, benzyl and phenyl.

In contrast to α-hydroxyacids the ester form of α-ketoacids is known to be therapeutically effective for cosmetic and dermatologic conditions and disorders. For example, while ethyl acetate is reported to have a minimal effect, ethyl pyruvate is therapeutically very effective. Although the real mechanism for such difference is not known, it has been speculated that the ester form of an α-ketoacid is chemically and/or biochemically very reactive, and a free acid form of the α-ketoacid is released in the skin after the topical application.

The representative α-ketoacids and their esters which may be useful in compositions of this invention include:
1. 2-Ketoethanoic acid (Glyoxylic acid)
(H) CO COOH
2. Methyl 2-ketoethanoate
(H) CO COOCH$_3$
3. 2-Ketopropanoic acid (Pyruvic acid)
CH$_3$ CO COOH
4. Methyl 2-ketopropanoate (Methyl pyruvate)
CH$_3$CO COOCH$_3$
5. Ethyl 2-ketopropanoate (Ethyl pyruvate)
CH$_3$CO COOC$_2$H$_5$
6. Propyl 2-ketopropanoate (Propyl pyruvate)
CH$_3$ CO COOC$_3$H$_7$
7. 2-Phenyl-2-ketoethanoic acid (Benzoylformic acid)
C$_6$H$_5$ CO COOH
8. Methyl 2-phenyl-2-ketoethanoate (Methyl benzoylformate)
C$_6$H$_5$ CO COOCH$_3$
9. Ethyl 2-phenyl-2-ketoethanoate (Ethyl benzoylformate) C$_6$H$_5$ CO COOC$_2$H$_5$
10. 3-Phenyl-2-ketopropanoic acid (Phenylpyruvic acid)
C$_6$H$_5$CH$_2$ CO COOH
11. Methyl 3-phenyl-2-ketopropanoate (Methyl phenylpyruvate)
C$_6$H$_5$CH$_2$ CO COOCH$_3$
12. Ethyl 3-phenyl-2-ketopropanoate (Ethyl phenylpyruvate) C$_6$H$_5$CH$_2$ CO COOC$_2$H$_5$
13. 2-Ketobutanoic acid
C$_2$H$_5$ CO COOH
14. 2-Ketopentanoic acid
C$_3$H$_7$CO COOH
15. 2-Ketohexanoic acid
C$_4$H$_9$CO COOH
16. 2-Ketoheptanoic acid
C$_5$H$_{11}$ CO COOH
17. 2-Ketooctanoic acid
C$_6$H$_{13}$ CO COOH
18. 2-Ketododecanoic acid
C$_{10}$H$_{21}$CO COOH
19. Methyl 2-ketooctanoate
C$_6$H$_{13}$CO COOCH$_3$ The third type of active compound according to the present invention is chemically related to α-hydroxyacids or α-ketoacids, and can be represented by their names instead of the above two generic structures. The third type of active compound includes ascorbic acid, quinic acid, isocitric acid, tropic acid, trethocanic acid, 3-chlorolactic acid, cerebronic acid, citramalic acid, agaricic acid, 2-hydroxynervonic acid, aleuritic acid and pantoic acid.

Amino Polymer

A second essential element of the cosmetic compositions according to the present invention is that of a multi-amine functionalized polymer. The polymer must be capable of effectively neutralizing at least some of the active compounds thereby forming an amine salt thereof. Ordinarily the polymer will have a pH in water from about 7.5 to about 14. Amounts of the polymer will range from about 0.01 to 40%, preferably from about 0.1 to 20%, optimally between about 0.5 and 10% by weight. Advantageously, the molar equivalent weight ratio of active compound to polymer will be from about 50:1 to 1:10, preferably 20:1 to 1:5, more preferably from about 5:1 to 1:2, optimally from about 2:1 to 1:1. The polymer may have a structure commensurate with Formula I or II below:

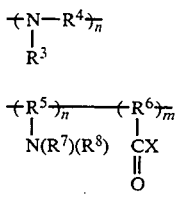

$$\begin{array}{c} +N-R^4\!\!+_n \\ | \\ R^3 \end{array} \quad (I)$$

$$\begin{array}{cc} +R^5\!\!+_n & +R^6\!\!+_m \\ | & | \\ N(R^7)(R^8) & CX \\ & \| \\ & O \end{array} \quad (II)$$

wherein:

$R^4$, $R^5$ and $R^6$ are independently $C_1$–$C_{12}$ radicals substituted or unsubstituted, branched or unbranched chains selected from the group consisting of alkylene, arylene, arylalkylene, alkylarylene and cycloalkylene radicals;

$R^3$, $R^7$ and $R^8$ are independently hydrogen or $C_1$–$C_{12}$ radicals selected from the group consisting of alkyl, cycloalkyl, aryl, phenyl, benzyl and hydroxyalkyl radicals;

$R^7$ and $R^8$ may also form with nitrogen a heterocyclic ring such as a pyridine, pyrrolidone, piperidine and piperazine ring;

X is $OR^3$ or $N(R^7)(R^8)$;

n and m together are integers of at least 2, preferably from 5 to 5000; and n and m separately are integers from 0 to 5000, preferably from 2 to 1000, optimally from 5 to 100.

Molecular weight of the polymers may range anywhere from about 500 up to 4 million, preferably from about 1,000 to 2 million, optimally from about 10,000 to 800,000 average molecular weight. These polymers may be obtained through condensation or free radical vinyl polimerization techniques. They may be homo- or co- polymers.

Illustrative of the polymers according to the present invention as defined in Formula I are:
poly(ethylenimine)
poly(propylenimine)
poly(aminophenylene)
poly(butylenimine)
diethylenetriamine
triethylenetetramine Illustrative of the polymers according to Formula II are:
poly(phenylamine)
poly(p-aminostyrene)
poly(o-aminostyrene)
poly(m-aminostyrene)
poly(p-dimethylaminostyrene)
poly(p-ditert-butylaminostyrene)
poly(vinylamine)
poly(vinylpyridine)
poly(diethylamino ethyl acrylate)
poly(diethylamino ethylacrylamide)
poly(dimethylamino ethylacrylate)
poly(dimethylamino ethylacrylamide)
poly(diethylamino ethyl methacrylate)
poly(diethylamino ethyl methacrylamide)
poly(vinylpyrrolidone/dimethylamino ethyl methacrylate)

Polymers of the present invention as herein defined are neither aminoacids nor amphoteric or polysaccharide substances.

Cosmetic compositions of the present invention will also include a pharmaceutically acceptable carrier in amounts from about 1 to about 95% by weight. The carrier may be an emollient, humectant, thickener and any combination thereof.

Emollient materials may either be silicone oils or organic esters.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl esters of fatty acids having 10 to 20 carbon atoms. Examples thereof include oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which cholesterol fatty acid esters are examples thereof.

Humectants of the polyhydric alcohol-type may also be included in the compositions of this invention. The humectant aids in increasing the effectiveness of the emollient, reduces scaling, stimulates removal of built-up scale and improves skin feel. Most especially for purposes of this invention, polyhydric alcohols enhance penetration of water-phase dissolved actives (e.g. the hydroxycarboxylic acids, alkyl lactates and antimicrobials). Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Of course, water is the most common humectant. Water may be present in amounts anywhere from about 1 to about 99%, preferably from about 25 to about 75% by weight.

Thickeners/viscosifiers in amounts up to about 5% by weight of the composition may also be included. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses (particularly hydroxypropyl cellulose), and cross-linked acrylic acid polymers such as those sold by B.F. Goodrich under the Carbopol trademark.

Solvents may also be included in cosmetic compositions of the present invention. Most commonly, the solvent is a $C_1$–$C_4$ monohydric alcohol especially ethanol. The monohydric alcohols may be present in amounts of from about 1 to about 99%, preferably from about 15 to about 70% by weight.

Cosmetic compositions of the present invention may be formulated in a variety of product forms. These forms may include lotions, creams, sticks, roll-on formulations, mousses, aerosol sprays, pad-applied formulations, and overnight peelable facial masks.

The following examples will more fully illustrate select embodiments of this invention. All parts, percentages and proportions referred to herein and in the appended claims are by weight unless otherwise indicated.

EXAMPLE 1

This Example illustrates a facial cleansing foam formulated in accordance with the present invention.

| FACIAL CLEANSING FOAM | |
|---|---|
| COMPONENT | WEIGHT % |
| Sodium Cocoyl Isethionate | 18.0 |
| L-Lactic Acid Neutralized with Poly(ethylenimine) | 5.5 |
| Sodium Lauroyl Sarcosinate | 3.0 |
| Glycol Stearate | 3.0 |
| PPG-5-Ceteth-10-Phosphate | 2.5 |
| Cetearyl Alcohol | 1.0 |
| Sorbitol | 1.0 |
| Linoleamide DEA | 1.0 |
| Mineral Oil | 0.8 |
| Beeswax | 0.7 |
| Ceresin | 0.4 |
| Sodium Borate | 0.3 |
| Methyl Paraben | 0.2 |
| Propyl Paraben | 0.2 |
| Water | qs |

EXAMPLE 2

This Example illustrates a skin care lotion formulated in accordance with the present invention.

| SKIN CARE LOTION | |
|---|---|
| COMPONENT | WEIGHT % |
| Glycerin | 15.0 |
| 2-Hydroxyoctanoic Acid neutralized with Poly(ethylenimine) | 12.0 |
| Stearic Acid | 10.0 |
| $C_{11}$–$C_{13}$ Isoparaffin | 10.0 |
| Glycol Stearate | 2.5 |
| Mineral Oil | 2.0 |
| Triethanolamine | 1.0 |
| Cetyl Alcohol | 1.0 |
| Dimethicone | 0.8 |
| DEA-Cetyl Phosphate | 0.3 |
| Magnesium Aluminum Silicate | 0.4 |
| Acetylated Lanolin Alcohol | 0.4 |
| Stearamide AMP | 0.3 |
| Methyl Paraben | 0.2 |
| Propyl Paraben | 0.2 |
| Fragrance | 0.2 |
| Carbopol 934 ® | 0.1 |
| Disodium EDTA | 0.1 |
| Water | qs |

EXAMPLE 3

This Example illustrates a deodorant stick formulated in accordance with the present invention.

| DEODORANT STICK | |
|---|---|
| COMPONENT | WEIGHT % |
| Propylene Glycol | 61.5 |
| Sodium Stearate | 5.4 |
| Ethylene Oxide/Propylene Oxide Copolymer | 4.8 |
| Glycolic Acid Neutralized with Poly(propylenimine) | 3.0 |
| Trichlosan | 0.3 |
| Colorant | 0.2 |
| Fragrance | 1.0 |
| Water | qs |

EXAMPLE 4

This Example illustrates a self-tanning lotion formulated in accordance with the present invention.

| SELF-TANNING LOTION | |
|---|---|
| COMPONENT | WEIGHT % |
| Propylene Glycol | 25.0 |
| Dihydroxyacetone | 3.0 |
| Polyacrylamide | 2.5 |
| Silicone Copolyol | 2.0 |
| Lactic Acid Neutralized with Poly(phenylenimine) | 1.5 |
| Methylparaben | 0.2 |
| Propylparaben | 0.2 |
| Fragrance | 0.2 |
| Water | qs |

EXAMPLE 5

This Example illustrates a body rub gel formulated in accordance with the present invention.

| BODY RUB GEL | |
|---|---|
| COMPONENT | WEIGHT % |
| Disodium Dimethicone Copolyol Sulfosuccinate | 10.0 |
| Jojoba beads | 4.0 |
| Cocoamidopropyl betaine | 3.0 |
| 2-Hydroxyoctanoic Acid Neutralized with Poly(ethylenimine) | 3.0 |
| Polysorbate 20 | 3.0 |
| Carbopol 934 ® | 1.5 |
| Benzyl Alcohol | 0.5 |
| Fragrance | 0.2 |
| DMDM Hydantoin | 0.2 |
| Sea Salt | 0.1 |
| Water | qs |

EXAMPLE 6

This Example illustrates a lipstick formulated in accordance with the present invention.

LIPSTICK

| COMPONENT | WEIGHT % |
| --- | --- |
| Castor Oil | 19.5 |
| Isopropyl Palmitate | 11.6 |
| Caprylic/Caproic Triglyceride | 10.0 |
| Lanolin | 7.0 |
| Red 21 Aluminum Lake | 7.0 |
| Candelilla Wax | 6.6 |
| Propylene Glycol Myristyl Ether Acetate | 6.0 |
| Glycerol | 5.0 |
| Water | 5.0 |
| Titanium Dioxide | 4.7 |
| Monoglyceride | 3.5 |
| Lanolin Oil | 2.5 |
| Ozokerite Wax | 2.5 |
| Ascorbic Acid Neutralized with Poly(p-aminostyrene) | 2.0 |
| Lecithin | 1.0 |
| Polybutene | 0.8 |
| Beeswax | qs |

EXAMPLE 7

This Example illustrates a sunscreen formulated in accordance with the present invention.

SUNSCREEN

| COMPONENT | WEIGHT % |
| --- | --- |
| Acetulan ® (cetyl acetate and acetylated lanolin alcohol) | 8.0 |
| Glycerine | 4.0 |
| 2-Hydroxylauric Acid Neutralized with Poly(butylenimine) | 3.5 |
| Stearic Acid | 2.0 |
| Dimethicone | 1.0 |
| Magnesium Aluminum Silicate | 1.0 |
| Octyl Methoxycinnamate | 1.0 |
| Oxybenzone | 1.0 |
| Cetyl Alcohol | 0.50 |
| Phenoxyethanol | 0.3 |
| Water | qs |

EXAMPLE 8

This Example illustrates an acne lotion formulated in accordance with the present invention.

ACNE LOTION

| COMPONENT | WEIGHT % |
| --- | --- |
| Benzoyl Peroxide | 7.0 |
| Glycerin | 3.0 |
| Glyceryl Monostearate | 3.0 |
| Smectite Clay | 2.5 |
| Glycolic Acid Neutralized with Poly(ethylenimine) | 2.0 |
| Stearyl alcohol | 1.0 |
| Isocetyl stearate | 1.0 |
| Preservative | 0.4 |
| Water | qs |

EXAMPLE 9

This Example illustrates an anti-dandruff shampoo formulated in accordance with the present invention.

ANTI-DANDRUFF SHAMPOO

| COMPONENT | WEIGHT % |
| --- | --- |
| TEA Lauryl Sulfate (40% Aqueous Solution) | 25.0 |
| Hamposyl L-30 (fatty acid sarcosinate) | 10.0 |
| Glycolic Acid Neutralized with Poly (o-aminostyrene) | 8.0 |
| Zinc Pyrithione | 2.2 |
| Hydroxypropyl methylcellulose | 1.3 |
| Modified Magnesium Aluminum Silicate | 1.0 |
| Water | qs |

EXAMPLE 10

This Example illustrates a hair growth stimulant formulated in accordance with the present invention.

HAIR GROWTH STIMULANT

| COMPONENT | WEIGHT % |
| --- | --- |
| Sodium Lauryl Ether Sulfate | 28.0 |
| Lactic Acid Neutralized with Poly (ethylenimine) | 12.0 |
| Lanolin Alcohol | 1.0 |
| Polysorbate 20 | 0.5 |
| Minoxidil ® | 0.3 |
| Preservative | 0.3 |
| Water | qs |

EXAMPLE 11

COMPARATIVE TESTS

This Example illustrates comparative tests formulated in accordance with the present invention.

Glycolic acid was chosen as representative of α-hydroxyacids and neutralized to form three different types of salts. The sodium (11A) and the triethanolammonium (11B) salts represent the known art. Polyethylenimine (11C) salts of glycolic acid are according to the present invention. The respective test formulas are outlined in Table I below.

TABLE I

| COMPONENT | TEST FORMULA (WT. %) | | |
| --- | --- | --- | --- |
| | 11A | 11B | 11C |
| Glycolic Acid | 11.4 | 11.4 | 11.4 |
| Sodium Hydroxide* | 6.0 | — | — |
| Triethanolamine (TEA)* | — | 22.3 | — |
| Poly(ethylenimine)* | — | — | 7.5 |
| Water | 82.6 | 66.3 | 81.1 |

*Present in an amount just sufficient to neutralize all of the glycolic acid.

A panel of seven subjects was chosen for evaluating the sting intensity of the different glycolate salts. Each of the panelists were prescreened to identify people especially sensitive to the sting aspects of α-hydroxyacids. Each formulation was applied around the nose and cheek of each panelist. Intensity of stinging was judged on a scale of 0 to 5 (shown as + in the performance table below). The higher the value, the greater the stinging intensity. Response was judged both at 1 and at 5 minutes subsequent to application of the formulation.

TABLE II

| PANEL-IST | STING INTENSITY TEST FORMULA (INTENSITY RATING) | | | | | |
|---|---|---|---|---|---|---|
| | 11A | | 11B | | 11C | |
| | 1 Min. | 5 Min. | 1 Min. | 5 Min. | 1 Min. | 5 Min. |
| 1 | +++ | +++ | +++ | +++ | + | 0 |
| 2 | + | + | + | + | 0 | 0 |
| 3 | + | + | + | ++ | 0 | 0 |
| 4 | +++ | ++ | ++ | +++ | + | + |
| 5 | ++ | ++++ | ++ | ++ | 0 | 0 |
| 6 | + | ++ | 0 | 0 | 0 | 0 |
| 7 | + | + | | | 0 | 0 |

The test results in Performance Table I establish that the polyethylenimine salt was significantly less stinging than either the sodium or triethanolammonium salts of glycolic acid.

The foregoing description and Examples illustrate selected embodiments of the present invention. In light thereof, various modifications will be suggested to one skilled in the art, all of which are within the spirit and purview of this invention.

What is claimed is:

1. A cosmetic composition comprising:
   (i) from about 0.01 to about 40% of an active compound selected from the group consisting of α-hydroxyacid, α-ketoacid and related compounds, wherein said α-hydroxyacid is represented by the following chemical structure:

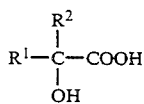

wherein $R^1$ and $R^2$ are selected from the group consisting of H, F, Cl, Br, alkyl and cyclic form having 5 to 6 ring members, and wherein $R^1$ and $R^2$ may be substituted with a substituent selected from the group consisting of OH, CHO, COOH and alkoxy groups having 1 to 9 carbon atoms, said α-hydroxyacid existing as a free acid or lactone form and as stereoisomers in D, L, and DL forms when $R^1$ and $R^2$ are not identical;

said α-ketoacid being represented by the following chemical structure:

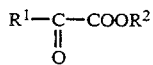

wherein $R^1$ and $R^2$ are selected from the group consisting of H, alkyl and cyclic form having 5 to 6 ring members, and wherein $R^1$ may be substituted with a substituent selected from the group consisting of F, Cl, Br, I, OH, CHO, COOH and alkoxy groups having 1 to 9 carbon atoms, said α-ketoacid existing as a free acid or an ester form; and said related compound being at least one member selected from the group consisting of ascorbic acid, quinic acid, isocitric acid, tropic acid, trethocanic acid, 3-chlorolactic acid, cerebronic acid, citramalic acid, agaricic acid, 2-hydroxynervonic acid, aleuritic acid and pantoic acid;

(ii) from about 0.01 to about 40% of a multi-amine functionalized polymer selected from the group consisting of poly(ethylenimine), poly(propylenimine), poly(aminophenylene), poly(butylenimine) diethylenetriamine, triethylenetetramine, poly(phenylamine) poly(p-aminostyrene), poly(o-aminostyrene), poly(m-aminostyrene), poly(p-dimethylaminostyrene), poly(p-ditert-butylaminostyrene), poly(vinylamine), poly(vinylpyridine), poly(diethylamino ethyl acrylate) poly(diethylamino ethylacrylamide), poly(dimethylamino ethylacrylate). poly(dimethylamino ethylacrylamide), poly(diethylamino ethyl methacrylate), poly(diethylamino ethyl methacrylamide) and poly(vinylpyrrolidone/dimethyramino ethyl methacrylate), said polymer neutralizing at least some of said active compound thereby forming an amine salt thereof; and from about 1 to about 95% by weight of a pharmaceutically acceptable carrier for said amine salt.

2. A composition according to claim 1 wherein the α-hydroxyacid is selected from the group consisting of glycolic acid, lactic acid, 2-hydroxyoctanoic acid, 2-hydroxy lauric acid and combinations thereof.

3. A cosmetic composition according to claim 1 wherein the polymer is selected from the group consisting of poly(ethylenimine), poly(propylenimine), poly(phenylenimine), poly(butylenimine) and mixtures thereof.

4. A cosmetic composition according to claim 1 wherein the α-hydroxyacid is glycolic acid and the polymer is poly(ethylenimine).

5. A method for treatment of dry skin, warts, nail infections, wrinkles, age spots and aging related skin changes, while minimizing any stinging irritation of the skin, by applying a composition comprising:
   (i) from about 0.01 to about 40% of an active compound selected from the group consisting of α-hydroxyacid, α-ketoacid and related compounds, wherein said α-hydroxyacid is represented by the following chemical structure:

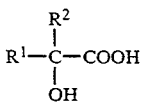

wherein $R^1$ and $R^2$ are selected from the group consisting of H, F, Cl, Br, alkyl having 1 to 25 carbon atoms and cyclic form having 5 to 6 ring members, and wherein $R^1$ and $R^2$ may be substituted with a substituent selected from the group consisting of OH, CHO, COOH and alkoxy groups having 1 to 9 carbon atoms, said α-hydroxyacid existing as a free acid or lactone form and as stereoisomers in D, L, and DL forms when $R^1$ and $R^2$ are not identical;

said α-ketoacid being represented by the following chemical structure:

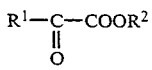

wherein $R^1$ and $R^2$ are selected from the group consisting of H, alkyl having 1 to 25 carbon atoms, and cyclic form having 5 to 6 ring members, and wherein $R^1$ may be substituted with a substituent selected from the group consisting of F, Cl, Br, I, OH, CHO, COOH and alkoxy groups having 1 to 9 carbon atoms, said α-ketoacid existing as a free acid or an ester form; and said related compound being at least one member selected from the group consisting of ascorbic acid, quinic acid, isocitric acid, tropic acid, trethocanic acid, 3-chlorolactic acid, cerebronic acid, citramalic acid, agaricic acid, 2-hydroxynervonic acid, aleuritic acid and pantoic acid;

(ii) from about 0.01 to about 40% of a multi-amine functionalized polymer selected from the group consisting of poly(ethylenimine), poly(propylenimine), poly(aminophenylene), poly(butylenimine), diethylenetriamine, triethylenetetramine, poly(phenylamine) poly(p-aminostyrene), poly(o-aminostyrene), poly(m-aminostyrene), poly(p-dimethylaminostyrene), poly(p-ditert-butylaminostyrene), poly(vinylamine), poly(vinylpyridine), poly(diethylamino ethyl acrylate) poly(diethylamino ethylacrylamide), poly(dimethylamino ethylacrylate), poly(dimethylamino ethylacrylamide), poly(diethylamino ethyl methacrylate), poly(diethylamino ethyl methacrylamide) and poly(vinylpyrrolidone/dimethylamino ethyl methacrylate), said polymer neutralizing at least some of said active compound thereby forming an amine salt thereof; and (iii) from about 1 to about 95% by weight of a pharmaceutically acceptable carrier for said amine salt.

6. A method according to claim 5 wherein the α-hydroxyacid is selected from the group consisting of glycolic acid, lactic acid, 2-hydroxyoctanoic acid, 2-hydroxy lauric acid and combinations thereof.

7. A method according to claim 5 wherein the polymer is selected from the group consisting of poly(ethylenimine), poly(propylenimine), poly(phenylenimine), poly(butylenimine) and mixtures thereof.

8. A method according to claim 5 wherein the α-hydroxyacid is glycolic acid and the polymer is poly(ethylenimine).

* * * * *